Sept. 7, 1943. R. L. BYRUM Plant Pat. 600
ROSE PLANT
Filed March 15, 1943
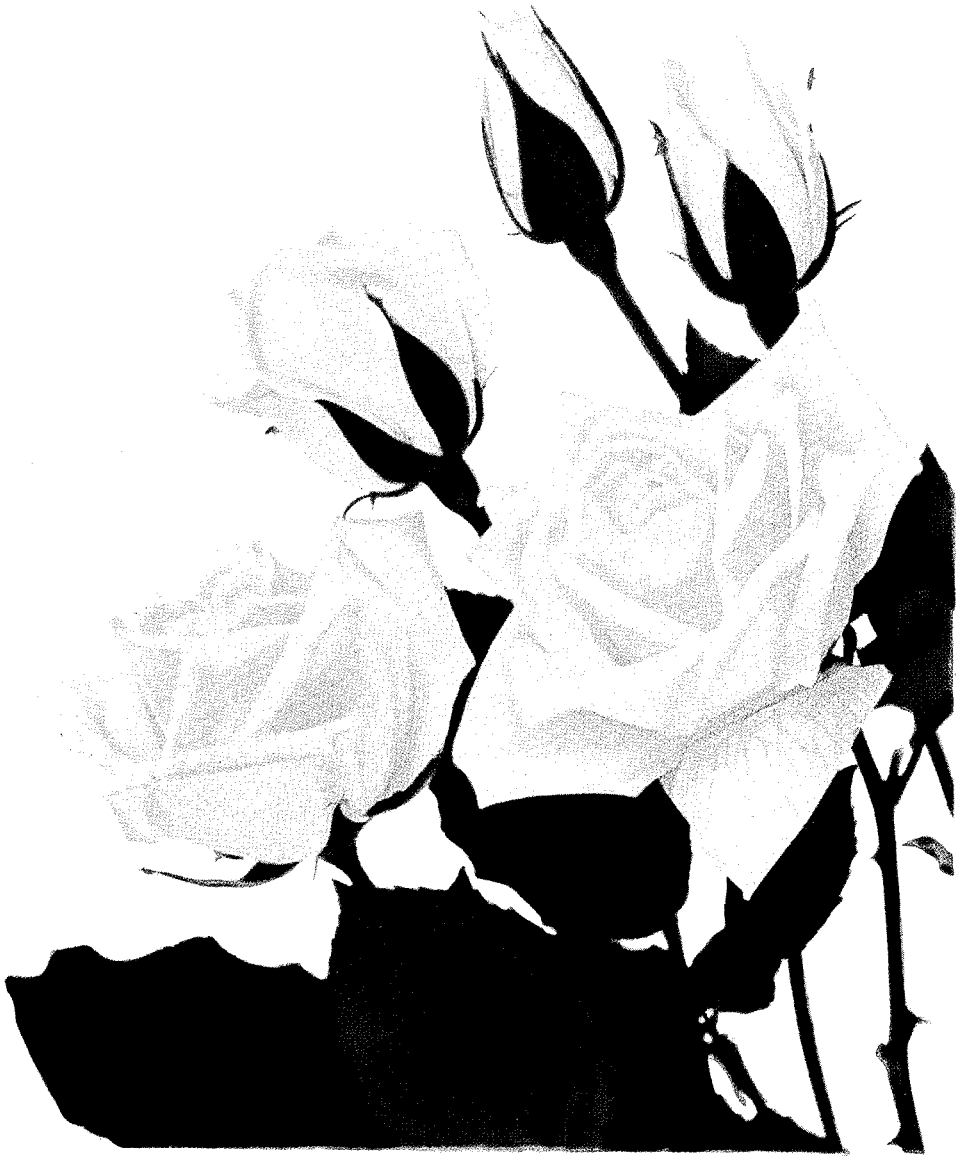
Inventor
Roy L. Byrum
By Robb & Robb
Attorneys Patented Sept. 7, 1943

Plant Pat. 600

UNITED STATES PATENT OFFICE

600

ROSE PLANT

Roy L. Byrum, Richmond, Ind., assignor to Joseph H. Hill Company, Richmond, Ind., a corporation of Indiana Application March 15, 1943, Serial No. 479,266

1 Claim. (Cl. 47—61)

The present invention relates to a new and distinct variety of rose plant of the hybrid tea class, having as its objective the improvement of an existing variety having certain known weaknesses.

The existing variety above referred to is known as "Geheimrat Duisberg" ("Golden Rapture" in the United States), a hybrid tea introduced into this country some years ago, a clear golden yellow rose, which by tests is shown to possess unsatisfactory weaknesses, such as weakness of growth, very little resistance to blackspot and mildew, and a great tendency to drop its foliage easily.

To overcome these and other undesired characteristics, this variety was crossed with an outstanding one well known to the trade as "Joanna Hill," resulting in a marked improvement of the deficiencies mentioned above accompanied by a number of other distinctive and desired qualities.

This new variety originating as stated here, while resembling its pollen parent, in that the blossoms are both in the yellow color range, the two colors are quite noticeable and distinct.

Moreover, "Golden Rapture" has very glossy foliage while this new variety is not at all glossy.

The thorns of this new variety are not as large as those of "Golden Rapture" and are different in color; the plant is more resistant to disease, as determined by observation during development; is very productive; does not drop its foliage easily, and develops long-pointed buds, so important in the type of roses designed for the cut flower trade and greenhouse forcing.

Other distinguishing characteristics reside in its free and abundant blooming habit, with large blooms occurring singly on strong stems, and of long lasting quality when used as cut flowers.

Asexual reproduction of this new variety shows the foregoing characteristics come true to form and are established.

The following is a detail description of the plant and flower of this new variety, all color terminology being in accord with Ridgway's Color Standard where indicated by plate numbers; otherwise ordinary dictionary meaning.

Type: Half hardy; tall bush; greenhouse; seedling; for cut flowers.
Class: Hybrid Tea.
Breeding: Seedling:
*Seed parent.*—"Joanna Hill."
*Pollen parent.*—"Geheimrat Duisberg."
Propagation: Holds its distinguishing characteristics through succeeding propagations by cuttings, grafting, and budding.

*Flower*

Locality where grown: Richmond, Indiana.
Flowers borne: Singly to stem; on strong, medium length stems.
Quantity of bloom: Free; abundant, in greenhouse.
Continuity: Continuous.
Fragrance: Moderate; tea.
Bud:
*Peduncle.*—Medium length; medium heavy; erect; Light Green; almost smooth; numerous green prickles.
*Before calyx breaks.*—*Size*—medium. *Form*—long pointed with a conspicuous neck; with foliaceous appendages on the surface of the bud; with much cut, bristle-like foliaceous parts extending beyond the tip of the bud equal to one-half or more of its length.
*As calyx breaks.*—*Color*—Buff Yellow, Plate IV.
*As first petal opens.*—*Size*—medium large. *Form*—long pointed. *Color*—Outside—Buff Yellow, Plate IV. Inside—Buff Yellow, Plate IV. *Opening*—opens up well.
Bloom:
*Size, when fully open.*—Medium large; 3½ to 4½ inches.
*Petalage.*—Double; from 30 to 35 petals.
*Form.*—High center; globular at first, becoming open; petals remaining at first loosely rolled outward; become later, at maturity, very loosely rolled outward.
Petals: Thick, with inside and outside shiny.
*Shape.*—Outside—obovate; with apex round. Intermediate—obovate; with apex round. Inside—obovate.

This description of a newly opened flower was made from a rose grown in a greenhouse during the month of April, 1942, at Richmond, Indiana:

*Color.*—Outside petal: outside surface—base: very light shading of Wax Yellow, Plate XVI, changing to Amber Yellow, Plate XVI. Inside surface—base: Primuline Yellow, Plate XVI, changing to Mustard Yellow, Plate XVI. Intermediate petal: outside surface—base: Wax Yellow, Plate XVI, changing to Amber Yellow, Plate XVI. Inside surface—base: Primuline Yellow, Plate XVI, changing to Mustard Yellow, Plate XVI. Inner petal: outside surface—base: Wax Yellow, Plate XVI, changing to Amber Yellow, Plate XVI. Inside surface—base: Primuline Yellow, Plate XVI, changing to Mustard Yellow, Plate XVI.

This description was made from a rose that was open for three days in a greenhouse in the month of April, 1942, at Richmond, Indiana:

*Color.*—Outside petal: outside surface—Straw Yellow, Plate XVI. Inside surface—Barium Yellow, Plate XVI. Intermediate petal: outside surface—Straw Yellow, Plate XVI. Inside surface—Barium Yellow, Plate XVI. Inner petal: outside surface—Straw Yellow, Plate XVI. Inside surface—Barium Yellow, Plate XVI.

*General color effect.*—Newly opened flower—Mustard Yellow, Plate XVI. Three days open—Barium Yellow, Plate XVI.

*Behavior.*—Persist.

*Flower longevity.*—As cut roses grown in greenhouse kept at living-room temperatures five to six days in April.

*Reproductive organs*

Stamens: Many; arranged regularly about pistils.

Filaments: Medium length; Yellow, reddish; most with anthers.

Anthers: Medium size; yellow, brown; all open at once.

Pollen: Abundant; gold.

Pistils: Many.

Styles: Uneven; medium length; thin; bunched.

Stigma: White.

Ovaries: Some protruding from calyx.

Sepals: Permanent; moderately short; spear-shaped; curled.

*Color.*—Inside—Biscay Green, Plate XVII, overlaid with brown fuzz. Outside—Biscay Green, Plate XVII.

Seeds: None as yet.

*Plant*

Foliage:

*Leaves.*—Compound of five to seven leaflets; very abundant; large; heavy; leathery.

*Leaflets.*—*Shape*—Ovoid, with apex acute; base, obtuse; margin simply serrate.

*Color.*—*Mature*—upper surface—Very Dark Green. Under surface—Moderately Light Green. *Young*—upper surface—Moderately Green Bronze. Under surface—Light Green Bronze.

*Rachis.*—*Medium heavy*—upper side—grooved; hairy. Under side—extremely smooth.

*Stipules.*—Medium length; very narrow; with moderately short points, turning out at an angle of less than 45°.

*Disease.*—Resistant to mildew and blackspot.

Growth:

*Habit.*—Upright; much branched.

*Growth.*—Free; vigorous.

*Canes.*—Medium heavy.

*Main stems.*—Green bronze. *Thorns*—several; medium length; hooked downward; with short round base. *Prickles*—few; brown. *Hairs*—none.

*Branches.*—Bright Green Bronze. *Thorns*—several; medium length; hooked downward; with short, narrow base. *Prickles*—none. *Hairs*—none.

*New shoots.*—Green Bronze Red. *Thorns*—several; medium length; hooked downward; with short, broad base. *Prickles*—none. *Hairs*—none.

I claim:

A new and distinct variety of hybrid tea rose plant characterized as to novelty by its free and vigorous growing habit, the heavy production of long-pointed buds developing into large blossoms borne singly on strong stems and of distinctive color in the yellow range, high resistance to mildew and blackspot, and persistency of its heavy, leathery foliage, substantially as shown and described.

ROY L. BYRUM.